United States Patent [19]

Cheslow

[11] 3,995,639
[45] Dec. 7, 1976

[54] DIAPER HAVING TAB FASTENER WITH AN ANCHORING LEG FOLDED ON BIAS

[75] Inventor: Ernest Cheslow, Glencoe, Ill.

[73] Assignee: Johnson & Johnson, New Brunswick, N.J.

[22] Filed: Dec. 19, 1975

[21] Appl. No.: 642,261

[52] U.S. Cl. ............................... 128/287; 128/284
[51] Int. Cl.² ......................................... A61F 13/16
[58] Field of Search ................ 128/284, 287, 290 R

[56] References Cited

UNITED STATES PATENTS

| | | | |
|---|---|---|---|
| 3,848,594 | 11/1974 | Buell | 128/284 |
| 3,921,639 | 11/1975 | Cepuritis | 128/287 |
| 3,954,106 | 5/1976 | Tritsch | 128/287 |

Primary Examiner—Aldrich F. Medbery

[57] ABSTRACT

A disposable diaper having a facing sheet defining a diaper inside surface for direction toward an infant and a backing sheet defining a diaper outside surface is provided with adhesive tabs having a free end and a digitated fixed end which includes at least two integral anchoring legs. Each leg is provided with an adhesive coating on one face thereof. At least one of the legs is folded over on a bias so that a portion of the adhesive-coated face thereof is juxtaposed to an adjacent portion of the same adhesive-coated face. The fixed end is permanently attached by means of the adhesive coatings to the diaper facing and backing sheets, at least one leg being attached to the facing sheet and the remaining legs being attached to the backing sheet. The free end of the tab has an adhesive coating on one face thereof, is releasably attached to a release region, and is separable from the release region to make the adhesive-coated free end of the tab available for use in securing the diaper about an infant.

16 Claims, 11 Drawing Figures

U.S. Patent  Dec. 7, 1976  Sheet 1 of 2  3,995,639
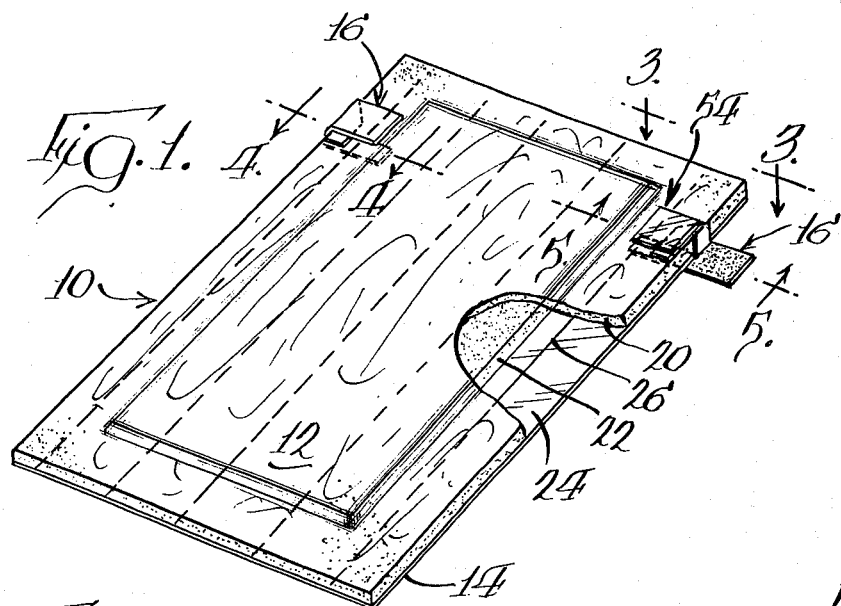
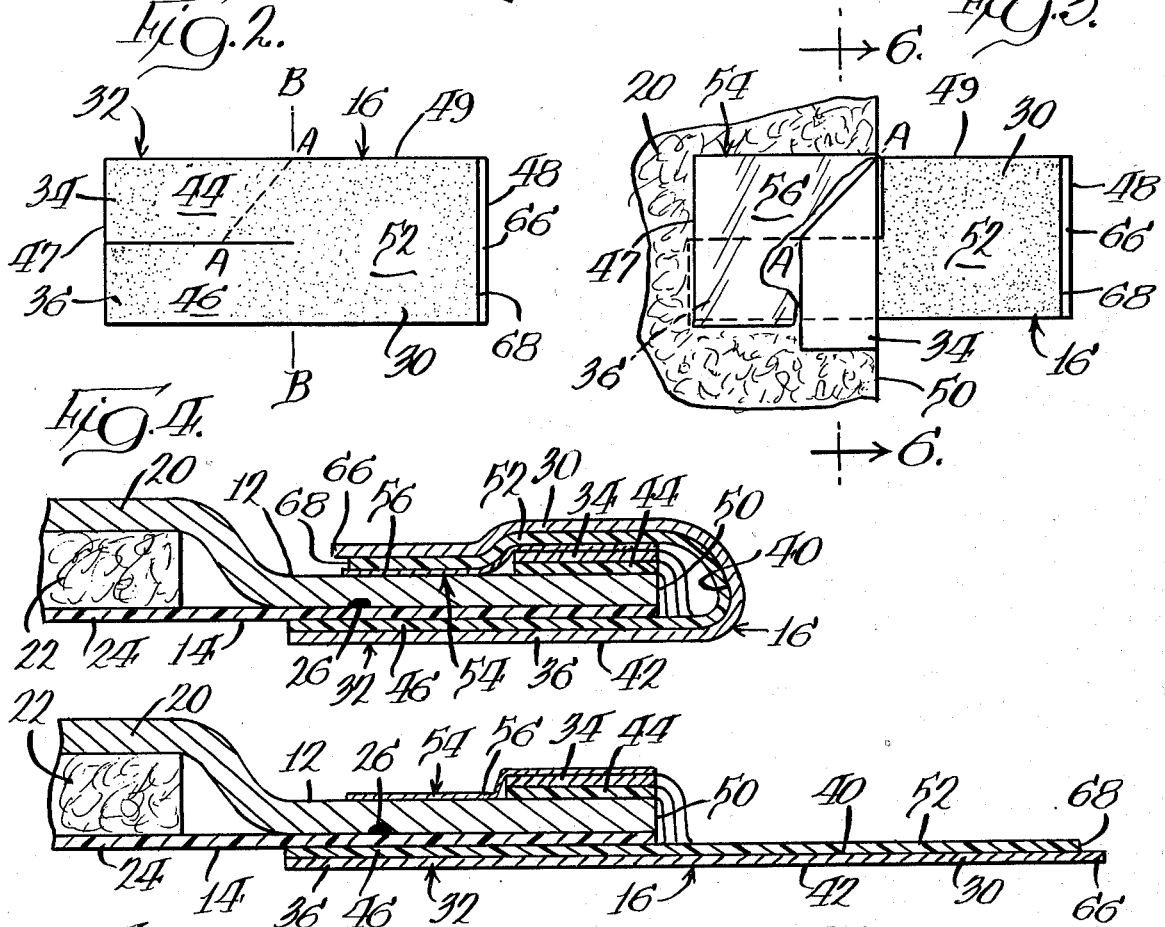
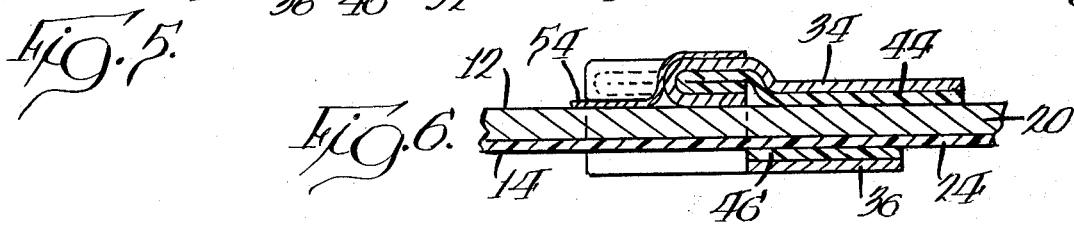

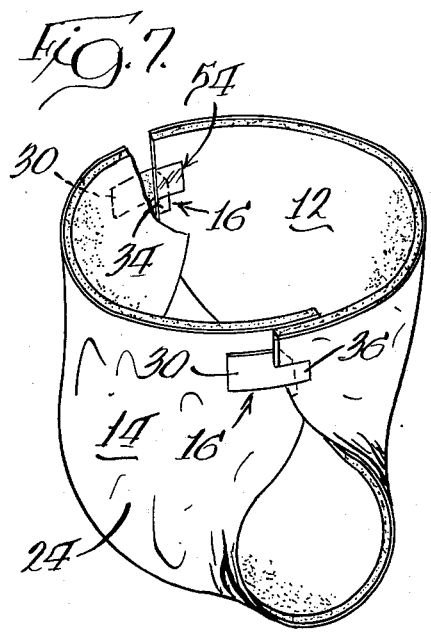
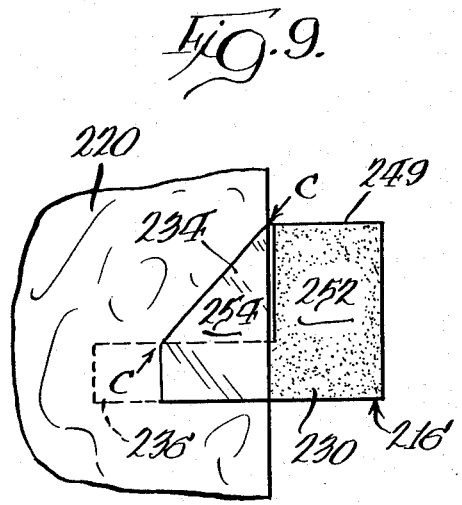
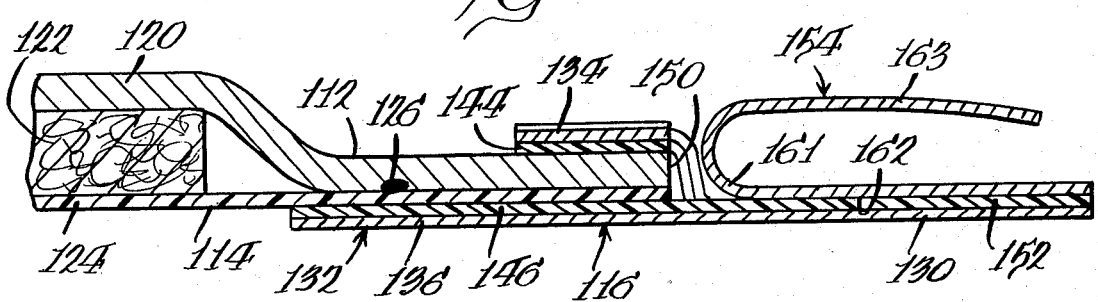
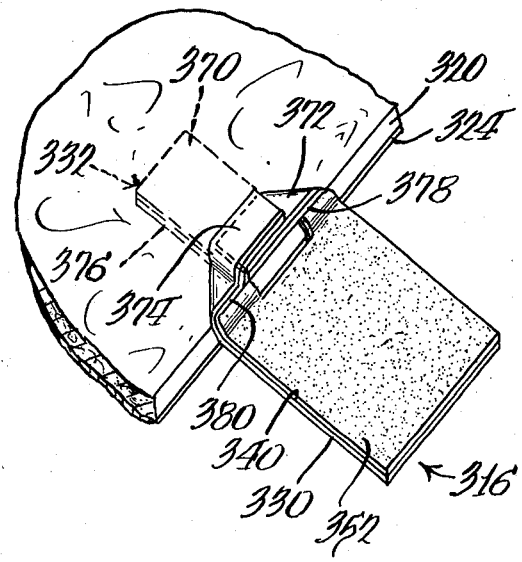
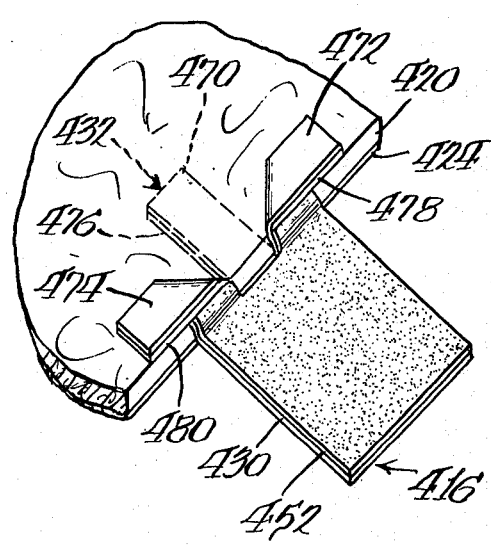

DIAPER HAVING TAB FASTENER WITH AN ANCHORING LEG FOLDED ON BIAS

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re.26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,646,937 to Gellert teaches a fastening tab which is provided with a release surface permanently bonded primarily to the inside surface of the diaper. One of the drawbacks of the Gellert arrangement is that in use the adhesive tape fasteners are permanently attached to only one surface of the diaper, generally the outside surface of the backing sheet, and thus the bond between one end of the tape fastener and the diaper backing sheet is subjected to all of the stresses exerted on the tape fastener during securement or as the infant moves about.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabric, may tear the facing fabric upon separation therefrom.

U.S. Pat. No. 3,776,234 to Hoey proposes to fold the tab over on itself at the diaper's edge and to adhesively attach a portion of the folded-over tab segment to an inwardly-folded margin of the diaper backing sheet in order to keep the tab flat against the diaper and thus from interfering with the manufacturing machinery and with the subsequent folding and packaging operations. This requires that the edge of the diaper backing sheet be folded over to present an attachment surface at the front or inside face of the diaper, and a relatively involved tab design is necessary for this purpose. Also, undesirable tearing of the diaper facing fabric may result if such a tab is inadvertently adhesively attached to the facing fabric of the diaper during manufacture.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two specially interconnected tape portions. Moreover, the turned up end of the reinforcing tape portion causes the folded configuration of the sealing tape to be somewhat bulky.

The adhesive fastener disclosed in U.S. Pat. No. 3,833,456 to Reed et al. can also be attached to both the front and back surfaces of a diaper to provide for force distribution over both surfaces. This particular fastener comprises two coextensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together. Since two substantially co-extensive webs are present, the fastener is bulky in the folded configuration, and is relatively expensive to manufacture.

A similar tape fastener is shown in U.S. Pat. No. 3,848,594 to Buell wherein the tape fastener is also attached to both the front and back surfaces of the diaper while having a securing portion attached to an adjacent section of the diaper, but has the disadvantage in that each tape fastener is comprised of two or more separate tape segments which are joined together so as to produce a common area of joinder for both fastener anchoring legs and the fastener securing portion, thereby adding complexities and expense to the manufacturing process, as well as requiring careful positioning during diaper manufacture.

SUMMARY OF THE INVENTION

According to the present invention, a diaper is provided with a single tape tab segment attached near each longitudinal margin of the diaper to secure the diaper about an infant. The tab has a free end and a digitated fixed end. The fixed end includes at least two integral anchoring legs, each anchoring leg being provided with an adhesive coating on one face thereof by means of which the fixed end is permanently attached to the facing and backing sheets of the diaper. At least one anchoring leg is folded over on a bias so that a portion of the adhesive-coated face thereof is juxtaposed to an adjacent portion of the same adhesive coated face. At least one anchoring leg is attached to the facing sheet and the remaining legs are attached to the backing sheet. The free end of the tab has a pressure-sensitive adhesive coating on one face thereof which is releasably attached to a release region, the tab being separable from the release region to make the adhesive-coated free end of the tab available for use in securing the diaper about an infant.

Three anchoring legs may be provided, with the middle leg being attached to the backing sheet and the flanking legs, comprising the folded-over legs, attached to the facing sheet. The flanking legs can be folded over so as to extend over the middle leg, or can be folded over and attached to the facing sheet outwardly of and extending away from the middle leg.

The release means may comprise a release coating which is printed or otherwise deposited on the facing sheet, a release strip having a release coating on one face thereof and an adhesive coating on the opposite face thereof by means of which the release strip is adhered to the facing sheet, a cover strip having a release coating on one face thereof, an exposed face of the folded-over anchoring leg, or other suitable means for providing releasable securement of the tab free end. Gripping means may also be provided on the tab to facilitate separation of the free end of the tab from the release means preparatory to fastening the diaper about an infant.

The tape tab fasteners of the present invention remain substantially flat against the diaper when in the folded configuration, do not interfere with the diaper manufacturing machinery and the subsequent folding and packaging operations, and in use provide good securement of the tab fastener to the diaper. Additional features of this invention include the utilization of an integral tape tab which is relatively easy to use and which provides permanent attachment of the tab to both the diaper facing sheet and backing sheet so that when stress is imposed on the free end which fastens the diaper, the stress is distributed between the facing sheet and the backing sheet, thereby reducing the possibility of undesirable rupture of the backing sheet.

BRIEF DESCRIPTION OF THE DRAWINGS

FIG. 1 is a perspective view, partially broken away to show interior detail, of an open unfolded diaper in accordance with one of the embodiments of this invention;

FIG. 2 is a plan view of the tab fastener in accordance with one of the embodiments of this invention;

FIG. 3 is an enlarged fragmentary plan view of the diaper of FIG. 1 taken along plane 3—3;

FIG. 4 is an enlarged fragmentary cross-sectional view of the diaper of FIG. 1 taken along plane 4—4;

FIG. 5 is an enlarged fragmentary cross-sectional view of the diaper of FIG. 1 taken along plane 5—5;

FIG. 6 is a fragmentary cross-sectional view of the diaper of FIG. 1 taken along plane 6—6 in FIG. 3;

FIG. 7 is a perspective view, partially broken away, of the diaper of FIG. 1 in a configuration assumed by the diaper when placed about an infant;

FIG. 8 is a fragmentary cross-sectional view, similar to FIG. 5, and illustrating an alternate embodiment of the invention;

FIG. 9 is a fragmentary plan view, similar to FIG. 3, and illustrating another embodiment of the invention; and FIGS. 10 and 11 are fragmentary perspective views illustrating additional embodiments of the invention.

DESCRIPTION OF THE PREFERRED EMBODIMENTS

In the following description, two digit numerals are used to refer to the embodiment illustrated in FIGS. 1–7, three digit numerals in the one hundred series are used to refer to the embodiment illustrated in FIG. 8, three digit numerals in the two hundred series are used to refer to the embodiment illustrated in FIG. 9, three digit numerals in the three hundred series are used to refer to the embodiment illustrated in FIG. 10, and three digit numerals in the four hundred series are used to refer to the embodiment illustrated in FIG. 11. The same last two digits in each numeral designate similar elements in the various embodiments.

Disposable diaper 10, illustrated in FIGS. 1 and 7, is of substantially quadrilateral configuration and presents inside surface 12 for direction toward an infant and outside surface 14 for direction away from the infant. Adhesive tab fastener means such as tab 16 is attached to diaper 10 at a marginal location for securing diaper 10 about an infant. As described in greater detail below, tab 16 is movable from a folded-over storage position illustrated in FIG. 4 to a working position which is illustrated in FIG. 5.

Referring first to FIGS. 1–7, diaper 10 comprises moisture-pervious facing sheet 20 which defines diaper inside surface 12, overlying a moisture-retaining absorbent pad 22, and backing sheet 24 which is made of a moisture-impervious material and defines diaper outside surface 14. Absorbent pad 22 can be somewhat smaller than the backing sheet 24 and is centrally disposed thereon; however, absorbent pad 22 can be made coextensive with backing sheet 24, if desired. Facing sheet 20 is substantially coextensive with backing sheet 24. Both the facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2–6, tab 16 is an integral elongated tape segment having free working end portion 30 and digitated fixed end portion 32 which includes at least two integral anchoring legs and which is integral with working end portion 30. The anchoring legs preferably are about equal in width and in the embodiment illustrated in FIGS. 1–7, comprise first and second legs 34, 36 which are formed by longitudinally cutting fixed end 32 to provide the desired number of anchoring legs. Tab 16 has a first face 40 which faces in the same direction as diaper inside surface 12 when tab 16 is in the working position, and an opposite second face 42. Anchoring legs 34, 36 are provided with an adhesive coating on one face thereof. For example, first and second legs 34, 36 are provided with adhesive coatings 44, 46 on the portion of first face 40 which is coterminous with the anchoring legs, as shown in FIGS. 4–6.

Digitated fixed end 32 is permanently attached to facing sheet 20 and backing sheet 24 at a marginal portion of diaper 10, at least one of the anchoring legs being permanently attached to facing sheet 20 and the remainder of the anchoring legs being permanently attached to backing sheet 24 by means of the adhesive coatings on the anchoring legs. As shown in FIGS. 4–6, digitated fixed end 32 receives a marginal portion of diaper 10 between the anchoring legs, at least one of the anchoring legs being adhesively attached to facing sheet 20 on diaper inside surface 12 and the remainder of the anchoring legs being adhesively attached to backing sheet 24 on diaper outside surface 14. Thus, first leg 34 can be adhesively attached to facing sheet 20 by means of adhesive coating 44, while second leg 36 is adhesively attached to backing sheet 24 by means of adhesive coating 46. Forces exerted on tab 16 can be thereby distributed to both the facing sheet 20 and backing sheet 24. Adhesive coatings 44, 46 can be made of a pressure-sensitive adhesive composition, a heat-activated or solvent-activated adhesive composition, or the like.

At least one of the anchoring legs is folded over on a bias so that a portion of the adhesive-coated face thereof is juxtaposed to an adjacent portion of the same adhesive-coated face. Thus, as illustrated in FIGS. 2 and 3, first anchoring leg 34 is folded over about fold line A—A, which traverses anchoring leg 34, to assume the configuration of FIG. 3. During manufacture, diaper 10 is received between second anchoring leg 36 and folded-over first anchoring leg 34 and both anchoring legs are adhesively attached thereto. Tab 16 has opposing terminal edges 47, 48 and the anchoring legs 34, 36 extend inwardly from terminal edge 47 of fixed end 32 to a location, such as line B—B which extends transversely across tab 16, intermediate fixed end 32 and free end 30. First anchoring leg 34 is folded-over on a bias about fold line A—A which preferably extends from line B—B along side edge 49 of tab 16 (FIG. 2) at about a 45° angle across first anchoring leg 34 toward terminal edge 47. In this particular embodiment, first anchoring leg 34 extends over the adjacent second anchoring leg 36 when leg 34 is folded over. Though a 45° angle is preferred, other angles will also serve the purpose of the present invention.

Referring to FIGS. 3 and 4, tab 16 is folded about the longitudinal edge 50 of diaper 10, and end portions 30 and 32 of tab 16 preferably are about equal in length. Free working end portion 30 provides a securement means for fastening diaper 10 about an infant and can be moved from the closed, storage position of FIG. 4 to the open, working position of FIG. 5. Free end 30 is provided with a pressure-sensitive adhesive coating 52 on first face 40 thereof, adhesive coating 52 facing in the same direction as diaper inside surface 12 when tab 16 is in the working position.

If desired, a marginal portion of backing sheet 24 can be received between anchoring legs 34, 36 in lieu of receiving the marginal portion of the entire diaper. In such a case, at least one of the anchoring legs can be positioned between facing sheet 20 and backing sheet 24, and can be adhesively attached to facing sheet 20. The remainder of the anchoring legs can be adhesively attached to backing sheet 24 on diaper outside surface 14. Thus, second anchoring leg 36 can have adhesive coating 46 on the portion of first face 40 which is coterminous with leg 36 and be adhesively attached to backing sheet 24 on diaper outside surface 14, and first anchoring leg 34 has adhesive coating 44 on the portion of second face 42 which is coterminous with leg 34 and is attached to facing sheet 20.

If desired, adhesive coatings 44, 46 on anchoring legs 34, 36 and adhesive coating 52 on free end 30 may comprise a continuous pressure-sensitive adhesive coating on first face 40 of tab 16.

Release means 54 is provided and is adapted to be releasably attached to adhesive coating 52 on free end 30. Release means 54 may comprise a release surface or layer, or a separable cover strip, and various embodiments of the release means are contemplated.

In the embodiment illustrated in FIGS. 1–7, release means 54 is carried by diaper 10 at a marginal location thereon and provides a release region facing in the same direction as diaper inside surface 12. Free end 30 of tab 16 is movable from the folded-over storage position of FIG. 4, wherein adhesive coating 52 on free end 30 is releasably adhered to release means 54, to the working position of FIG. 5 so as to make adhesive coating 52 available for use in securing diaper 10 about an infant.

The release means may comprise a ribbon segment or release strip having a release-coated surface on the face thereof which faces in the same direction as diaper inside surface 12 and which provides the release region, and an adhesive coating on the opposite face thereof by means of which the release strip is anchored to diaper inside surface 12 either directly or through a folded-over anchoring leg. Alternatively, the release means may comprise a release layer 56 which is a surface coating on a marginal portion of the diaper inside surface 12, and preferably comprises a silicone release compound, or the like, and may be transparent. The release strip or release layer preferably provides a release region of about the same width as tab 16 and is substantially coextensive with adhesive coating 52. However, the release region may have a greater width than tab 16.

In the embodiment illustrated in FIG. 8, release means 154 comprises a cover strip 161 which is provided with a release coating on face 162 thereof which is contiguous with adhesive coating 152. The release coating is substantially coextensive with at least the free end 130 of tab 116 and is removable therefrom. The inner end of cover strip 161 is preferably folded back on itself so as to provide end segment 163 which can be easily grasped to remove cover strip 161 from free end 130 of tab 116.

In some adhesive tapes, one face has an adhesive coating and the opposite face has release properties. By employing a tape of this type for tab 216, the portion of second surface 242 which is coterminous with leg 234 is provided with release properties and comprises release means 254, as illustrated by tab 216 in FIG. 9. A small corner portion of adhesive-coated free end 230 may adhere to facing sheet 220 adjacent fold line C—C but will not significantly reduce the overall holding capacity of adhesive-coated free end 230. In this embodiment, free end 230 preferably is shorter than fixed end 232, and leg 236 is attached to the backing sheet.

Referring to FIG. 10, fixed end 332 of tab fastener 316 includes three anchoring legs which preferably are about equal in width and comprise a middle leg 370 and at least two flanking legs 372, 374. First face 340 of tab 316 is coated with adhesive, legs 370, 372, 374 being provided with adhesive coatings 376, 378, 380, respectively, and free end 330 has adhesive coating 352. Middle leg 370 is attached to backing sheet 324 by means of adhesive coating 376, and flanking legs 372, 374 comprise the folded-over legs. Flanking legs 372, 374 are folded over so as to extend over middle anchoring leg 370 and are attached to facing sheet 320 by means of adhesive coatings 378, 380.

The embodiment illustrated in FIG. 11 is substantially similar to FIG. 10, except that flanking legs 472, 474 are folded over so as to extend away from middle anchoring leg 470 and are attached to facing sheet 420 outwardly of middle leg 470 by means of adhesive coatings 478, 480.

Any of the aforementioned release means can be utilized for protecting the pressure-sensitive adhesive coatings 352 and 452 on the respective free working ends of tab fasteners 316 and 416 prior to use.

In general, where the release means such as region 54 is provided on diaper inside surface 12, it is desirable to provide a gripping means to facilitate in separation of free end 30 of tab 16 from the release means preparatory to fastening the diaper about an infant. As is shown in FIGS. 2–5, free end 30 of tab 16 can be provided with a protruding portion 66 which extends beyond outermost margin or edge 68 of adhesive coating 52, whereby outwardly extending portion 66 provides a gripping means for removing free end 30 from the release means when fastening diaper 10 about an infant. Alternatively, the release means which comprises the release strip 56 can be provided with a longitudinal dimension which is greater than the longitudinal dimension of the free end 30 to enable a user to more easily grasp free working end 30. These and other modifications may be simultaneously used to facilitate gripping the terminal edge 48 of free end 30.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet and the like. Particularly preferred are webs which are oriented along the narrow dimension of the tab or webs which have filament reinforcements therein.

The pressure-sensitive adhesive layers such as adhesive coating 52 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips 56 can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75 to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd$^2$ and densities of less than 0.15 g./cc., generally in the range between 0.05 and 0.1 g./cc. The dry strength of the facing sheet for a fabric having a weight of about 1.5 oz./yd$^2$. is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd$^2$.

In addition, facing sheet 20 can be formed of a non-apertured, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re.26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling free end portions 30 away from their temporary engagement with the release means, exposing adhesive coating 52 which was releasably adhered to release means 54 and removable therefrom. The tabs are then used to secure the diaper in the desired position by simply urging the pressure-sensitive adhesive surfaces in contact with the adjacent outer surface of the diaper. The applied diaper assumes the configuration illustrated in FIG. 7.

The adhesion of at least one bias-folded anchoring leg of the tape segment to the exterior of the backing sheet provides assurance that the tape segment cannot easily be peeled off from its permanent attachment to the diaper edge. When a tape segment is adhered in the conventional manner at its fixed end to the exterior of the backing sheet at its margin, it can be peeled off by swinging its free end about until it is almost back to back with the fixed end and then applying a force in a direction toward the middle of the diaper, almost 180° from the direction of the forces normally applied to the tape segment.

In the tape segment of the present invention, the application of such a force would not result in peeling because while the straight anchoring leg or legs are pulled in a direction which would ordinarily result in peeling, the bias-folded anchoring leg or legs are being pulled at right angles to their length and require substantially more force to be pulled away from the backing sheet.

The foregoing description and the drawing are illustrative but are not to be taken as limiting. Still other variations and modifications are possible without departing from the spirit and scope of the present invention. For example, one of the anchoring legs such as leg 34 can be interposed between facing sheet 20 and backing sheet 24 and can be provided with an adhesive coating on both faces thereof, whereby one of the anchoring legs is attached to both facing sheet 20 and backing sheet 24, and the other anchoring leg is attached to facing sheet 20 or backing sheet 24.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:
   an integral elongated tape segment attached to said diaper at a marginal location thereof, having a free working end and a fixed end including at least two anchoring legs, each of said anchoring legs having an adhesive coating on one face thereof;
   a pressure-sensitive adhesive coating on one face of said free working end; and
   release means on the diaper for releasable attachment to said adhesive coating on said free working end;
   at least one of said anchoring legs being folded over on a bias so that a portion of the adhesive-coated face thereof is juxtaposed to an adjacent portion of the same adhesive-coated face and the remainder of the same adhesive-coated face is available for permanent attachment to the diaper;
   said tab fastener means being permanently attached to the facing sheet and backing sheet at a marginal location of said diaper by means of said anchoring legs, at least one of said legs being permanently attached to said facing sheet and the remainder of said anchoring legs being permanently attached to said backing sheet by means of said adhesive coatings;
   said free end being separable from said release means to make said adhesive-coated free end of said tape segment available for use in securing said diaper about an infant.

2. The disposable diaper as defined in claim 1 wherein said fixed end is provided with a pair of anchoring legs which receive a marginal portion of said diaper therebetween, one of said anchoring legs being attached to said facing sheet on the diaper inside surface and the other of said anchoring legs being attached to said backing sheet on the diaper outside surface.

3. The disposable diaper as defined in claim 2 wherein said folded-over anchoring leg is attached to said facing sheet.

4. The disposable diaper as defined in claim 1 wherein said fixed end receives a marginal portion of said backing sheet between said anchoring legs, wherein at least one of said anchoring legs is positioned between said facing sheet and said backing sheet and is adhesively attached to said facing sheet, and wherein the remainder of said anchoring legs are adhesively attached to said backing sheet on the diaper outside surface.

5. The disposable diaper as defined in claim 1 wherein said tape segment has opposing terminal edges, said fixed end is divided lengthwise to define anchoring legs which extend inwardly from the terminal edge of said fixed end to a location intermediate said fixed end and said free end, and wherein each of said folded-over anchoring legs is folded over so as to extend over an adjacent anchoring leg.

6. The disposable diaper as defined in claim 1 wherein said fixed end includes a middle anchoring leg and at least two anchoring legs flanking said middle leg, wherein said flanking legs are folded-over, and wherein said middle leg is attached to said backing sheet and said flanking legs are attached to said facing sheet.

7. The disposable diaper as defined in claim 6 wherein each of said flanking anchoring legs is folded over so as to extend away from said middle anchoring leg.

8. The disposable diaper as defined in claim 6 wherein each of said flanking legs is folded over so as to extend over said middle anchoring leg.

9. The disposable diaper as defined in claim 1 wherein said adhesive coating on said anchoring legs is a pressure-sensitive adhesive coating and said adhesive coatings on said free end and said anchoring legs together provide a continuous adhesive coating on one face of said tape segment.

10. The disposable diaper as defined in claim 1 wherein said release means comprises a cover strip provided with a release coating on one face thereof which is substantially coextensive with at least said free end of said tape segment and is removable therefrom.

11. The disposable diaper as defined in claim 1 wherein said release means is carried by said diaper at a marginal location thereon and provides a release region facing in the same direction as said diaper inside surface,
   said free end being movable from a folded-over storage position wherein said free end is releasably adhered to said release region to a working position wherein said adhesive-coated free end of said tape segment is available for use in securing said diaper about an infant.

12. The disposable diaper as defined in claim 11 wherein said release means comprises a ribbon segment carried by said diaper and provided with a release coating substantially coextensive with said free end of said tape segment and facing in the same direction as said diaper inside surface.

13. The disposable diaper as defined in claim 11 wherein said release means is a release coating on a portion of said diaper inside surface.

14. The disposable diaper as defined in claim 13 wherein said release coating comprises a silicone release compound.

15. The disposable diaper as defined in claim 11 wherein a portion of said free end projects beyond the outermost edge of said adhesive coating carried by said free end, whereby said projecting portion provides a gripping means for separating said tape segment from said release means when fastening said diaper about said infant.

16. The disposable diaper as defined in claim 11 wherein the opposite surface of said folded-over anchoring leg is provided with release properties and comprises said release means.

* * * * *